United States Patent [19]
Baker et al.

[11] Patent Number: 4,943,435
[45] Date of Patent: Jul. 24, 1990

[54] PROLONGED ACTIVITY NICOTINE PATCH

[75] Inventors: Richard W. Baker, Palo Alto; Frank Kochinke, Fremont; Carl Huang, Palo Alto, all of Calif.

[73] Assignee: Pharmetrix Corporation, Menlo Park, Calif.

[21] Appl. No.: 264,397

[22] Filed: Oct. 28, 1988

Related U.S. Application Data

[63] Continuation-in-part of Ser. No. 105,549, Oct. 5, 1987, Pat. No. 4,839,174.

[51] Int. Cl.$^5$ .............................................. A61L 15/00
[52] U.S. Cl. .................................... 424/448; 424/449; 424/486; 128/156; 128/632; 131/335
[58] Field of Search ............... 424/448, 449, 486; 128/156, 632; 131/335

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,742,951 | 7/1973 | Zaffaroni | 128/268 |
| 3,797,494 | 3/1974 | Zaffaroni | 128/268 |
| 3,996,934 | 12/1976 | Zaffaroni | 128/268 |
| 4,597,961 | 7/1986 | Etscorn | 424/28 |
| 4,624,665 | 11/1986 | Nuwayser | 424/448 |
| 4,627,429 | 12/1986 | Tsuk | 128/156 |
| 4,638,043 | 1/1987 | Szycher et al. | 424/449 |
| 4,687,481 | 8/1987 | Nuwayser | 424/449 |
| 4,706,676 | 11/1987 | Peck | 128/632 |
| 4,715,387 | 12/1987 | Rose | 131/335 |

FOREIGN PATENT DOCUMENTS 3438284 7/1985 Fed. Rep. of Germany .
61-251619 8/1986 Japan .

OTHER PUBLICATIONS

J. E. Rose et al., "Transdermal Administration of Nicotine," *Drug and Alcohol Dep.*, 13, 209–213, 1984.
J. F. Komerska, "Urethane Films—Transdermal Opportunities," J. Plastic Film and Sheeting, 3 58–64; 1987.

Primary Examiner—Henry F. Epstein
Assistant Examiner—P. S. Ryan
Attorney, Agent, or Firm—A. J. Castro; J. Farrant

[57] ABSTRACT

A transdermal patch for delivering nicotine for prolonged periods of 12–24 hours. The patch includes a rate-controlling membrane or monolith to keep the nicotine flux within useful and safe limits. The patch is typically replaced once a day, and can be used for smoking cessation therapy or in other situations where systemic nicotine delivery is indicated.

22 Claims, 8 Drawing Sheets

PROLONGED ACTIVITY NICOTINE PATCH

CROSS REFERENCE TO RELATED APPLICATIONS

This application is a continuation-in-part of U.S. patent application Ser. No. 105,549, filed Oct. 5, 1987 U.S. Pat. No. 4,839,174.

FIELD OF THE INVENTION

The invention relates to a transdermal patch for administering nicotine. More particularly, the invention concerns patches that can deliver an appropriate dosage of nicotine for a period of a day or more.

BACKGROUND OF THE INVENTION

Delivery of drugs by the transdermal route has been known to be theoretically possible for many years. The earliest developed transdermal patches were medicated bandages, usually with the drug mixed into the adhesive, designed to bring a known quantity of drug to a known area of skin for a known time. Such devices do not control the rate at which the drug is released. Controlled release transdermal patches rely for their effect on delivery of a known flux of drug to the skin for a prolonged period of time, measured in hours, days or weeks. Two mechanisms are used to control the drug flux from the patch: either the drug is contained within a drug reservoir, separated from the skin of the wearer by a synthetic membrane, through which the drug diffuses; or the drug is held dissolved or suspended in a polymer matrix, through which the drug diffuses to the skin. Patches incorporating a reservoir and membrane will deliver a steady drug flux across the membrane as long as excess undissolved drug remains in the reservoir; matrix or monolithic devices are typically characterized by a falling drug flux with time, as the matrix layers closer to the skin are depleted of drug. To date limited commercial exploitation of the transdermal administration route has been achieved, because of the many practical problems to be overcome with real systems. The skin is an effective barrier against the majority of drugs. Unless the delivery device is made unacceptably large, or the natural skin permeation rate of the drug is increased, then the drug flux across the skin is inadequate for useful therapy. Thus although in theory any drug might be delivered by this route, serious investigation of candidate drugs has been limited to a few where there are strong indications for transdermal use, namely: small molecular size; short half-life; rapid metabolization by the liver, rapid degradation in the GI tract; other problems with oral administration; high in vivo skin permeability; and high potency, i.e. small effective therapeutic dose. Despite active work in the field since at least 1970, at present commercial patches are available for delivery of only four drugs: nitroglycerin, scopolamine, clonidine, and estradiol.

The U.S. Surgeon General has determined that cigarette smoking is a major risk factor in coronary heart disease and is the cause of approximately 30% of all cancer deaths. However, it is very difficult to give up smoking, and any smoking cessation therapy has to deal with both the pharmacological and the psychological dependence on cigarettes. Separating the treatment of these two factors is an approach that has been tried with modest success, for example by satisfying the pharmacological craving with nicotine pills or chewing gum, while treating the psychological addiction independently. To date, the best results have been obtained with nicotine chewing gum, which achieves direct delivery to the systemic circulation by buccal absorption. However, chewing gum formulations taste bad, may lead to mouth ulcers and heartburn, cannot be used effectively by denture wearers, and depend entirely on the patient following the prescribed chewing regime. Other difficulties associated with oral administration include stomach upsets, nausea, rapid nicotine degradation, and irregular and unpredictable blood plasma levels.

Nicotine is very volatile, highly lipid soluble, and is known to permeate the skin easily, as happens for instance in the case of green tobacco sickness. The concept of applying the teachings of transdermal drug therapy to the delivery of nicotine has been recognized, and various research programs in the area, exemplified by the references below, have been undertaken.

German Patent Disclosure DE No. 3438284 discusses the general idea of delivering nicotine transdermally, and mentions that nitroglycerin is now available by the transdermal route.

Japanese Laid Open Application No. 61-251619 describes transdermal nicotine delivery using adhesive tapes in which 2-10% nicotine is mixed with the adhesive material. Nicotine delivery is controlled by the skin permeability. The tape is applied to the skin in strips about 70 $cm^2$ in area.

U.S. Pat. No. 4,597,961 discloses a transdermal patch with a reservoir of nicotine and a microporous membrane to control the nicotine flux. Patches of this design can be effective for periods up to 45 minutes.

A paper by J. E. Rose et al., "Transdermal Administration of Nicotine", *Drug and Alcohol Dependence*, 13, 209–213 (1984) discusses the physiological effects observed as a result of directly applying an aqueous solution containing 9 mg of nicotine to the skin, and covering the treated area with occlusive tape. Noticeable effects were observed for two hours.

There are substantial problems to be overcome in developing a transdermal nicotine system. First, at room or body temperature, nicotine is a volatile, reactive liquid and a strong solvent. Many of the common materials from which components of patches, such as backings, adhesives, membranes, matrices and peel strips, are made, are dissolved, attacked or degraded by nicotine. For example, adhesives become stringy, lose their tackiness, or become so heavily loaded with nicotine that they deliver a huge burst of nicotine when applied to the skin. Typical grades of polyisobutylene, acrylate or silicone-based adhesives behave this way when exposed to nicotine for periods as little as one week. Polymers that swell significantly, disintegrate, or dissolve completely in the presence of liquid nicotine include many grades of polyvinyl chloride, polycarbonate, polystyrene, polyethylene terephthalate, polybutyrate, polyurethane, ethylene-vinyl acetate copolymers, except those with low percentages of vinyl acetate, and Saran (polyvinylidene chloride). Polymers that can withstand physical or chemical attack frequently exhibit high nicotine permeabilities, making retention of nicotine within the system a problem. For example, ethylene vinyl acetate with vinyl acetate content less than 10% is not visibly attacked or dissolved by nicotine. However, the nicotine permeability through a 100–150 $\mu m$ thick film of this material is greater than 200 $\mu g/cm^2 \cdot h$. Even Saran ®, frequently the material of choice in situations where maximum barrier properties are required, exhibits a permeability for nicotine of 8 μg.100 μm/cm².h. From this exemplary discussion, it can be seen that designing a practical transdermal patch capable of both holding its nicotine load and dispensing it at an appropriate rate is a challenging problem. Some of the individual problems that must be resolved include:

1. Find a membrane or matrix material that is nicotine resistant or compatible.
2. Find a membrane or matrix material that can give a safe, useful in vitro nicotine flux in the present context, i.e. neither excessively high nor low when compared to the skin flux.
3. Find a nicotine-resistant adhesive with acceptable flux characteristics.
4. Find materials for backings and peel strips that are nicotine resistant and nicotine-impermeable.
5. Design a storage system that gives the patch a reasonable shelf-life.

Acceptable answers to these problems depend on the type of patch required. A non-controlled release patch, in other words one that occlusively covers a known area of skin, but permits uncontrolled exposure of that skin to nicotine, is less difficult to develop than one that meters the nicotine flux to the skin. The tape described in Japanese Laid Open Application No. 61-251619 is representative of this type of system. Such a patch cannot hold more than a low percentage loading of nicotine, and thus must cover a very large area of skin to be effective for even relatively short periods. In general, the smaller and more inconspicuous is a patch, the better is it accepted by patients. Therefore, patches that need to cover as much as 70 cm² of skin, as described in the Japanese application, are not well received by patients.

A system that can hold and deliver sufficient nicotine to replace the plasma level obtained from smoking a single cigarette is also less difficult to develop than one that must regulate a nicotine load 20 or more times greater. U.S. Pat. No. 4,597,961 is representative of the single cigarette approach. The patches described therein are either non-controlled release embodiments designed to hold the nicotine load in occlusive contact with the skin, or controlled release embodiments where the nicotine flux is regulated to some extent by a microporous membrane. This approach is effective for short periods, but nicotine can pass through the microporous membrane with minimal resistance, so that the system cannot last longer than about 45 minutes.

Both these approaches are useful, although neither can exploit the real benefits of controlled release transdermal therapy. In general, one of the recognized advantages of transdermal therapy as opposed to other drug administration techniques is the simplicity of the dosage regime. A patient using a transdermal patch is less likely to encounter compliance problems than one who is required to swallow pills two or three times a day, subject himself to percutaneous infusion or injection, etc. Also a transdermal patch that has to be changed regularly once a day or once a week, for example, is preferred over one that has to be replaced several times a day, twice a week or on an irregular schedule. Another major advantage of continuous transdermal delivery is that the blood plasma levels of the delivered agent remain relatively steady. In this way, the periodic fluctuations between plasma levels above the safe threshold and below the efficacy threshold that are often seen with oral tablets or injections are eliminated, as are the "highs" associated with addictive substances.

The reasons that currently available transdermal nicotine systems are not prolonged-effect, controlled-release systems are twofold, and both relate to the properties of nicotine. First, as already discussed, nicotine's low melting point and activity make it a good candidate for transdermal administration because it is easy to get through the skin. Skin is a very impermeable membrane, with resistance characteristics equivalent to a silicone rubber layer 10 mm thick. Therefore, substances that can permeate the skin easily can permeate most synthetic polymer films even more easily. Consequently it is a matter of real difficulty, and to applicants' knowledge a previously unsolved problem, to find materials and components, and to make systems, that can hold sufficient nicotine for prolonged periods, and to release that nicotine in a safe, controlled fashion.

The second issue that hampers the development of prolonged-activity systems relates to the clinical properties of nicotine, specifically skin irritation and toxicity. Nicotine is a known skin irritant, and a patch that exposes the skin to raw nicotine for any length of time is unacceptable. More importantly, nicotine is a very toxic substance. The lethal unit dose for an average adult is about 60 mg; one cigarette delivers about 1 mg nicotine. Therefore a patch that is to be effective for 12 or 24 hours, for an average smoker, must contain a nicotine load that is 50% or more of the average lethal dose. A single patch may contain a lethal dose if tampered with or ingested by a child, for example. Thus safety is a major concern. In addition to the purely technological problems already discussed, then, a system that contains a high nicotine load must also be able to control release of that load in such a way that an individual using the patch on his skin is never exposed to a toxic dose. In addition, opportunities for accidental or deliberate misuse must be minimized if possible. Based on these considerations, it is clear that an effective, safe long-acting system must be more than a system of the types exemplified in U.S. Pat. No. 4,597,961 or Japanese Laid Open Application No. 61-251619, modified to hold a bigger nicotine load.

An additional clinical factor to be taken into account is the addictive nature of nicotine. The powerful morning craving for a cigarette experienced by smokers is a manifestation of the very low nicotine plasma level that occurs after 8 to 12 hours without smoking. A regime that can sustain through the night a nicotine plasma level that reduces or eliminates that craving would thus be a breakthrough in smoking cessation therapy. Chewing gums, oral administration, or short-term transdermal patches fail in this respect.

In summary, then, a preferred transdermal regime is one in which a low, steady dose of nicotine is maintained throughout the day and/or night by a single patch application. However, the type of patch that can provide such a regime is large quantity of nicotine, must retain that nicotine throughout its shelf life, and must release it in a safe and controlled manner when applied to the skin. Extensive discussion above is intended to make clear the particular difficulties that are encountered in the design and development of a transdermal nicotine patch, especially one that is effective for prolonged periods. Recognizing the advantages that could be offered by a hypothetical transdermal system is altogether a different matter than possessing the technology to enable a workable system to be made. And the knowledge of systems that are non-controlled release, or are effective for short periods, is altogether a different matter than possession of the technology to provide a useable system that can be effective for periods of up to a day or more. To the applicants' knowledge a transdermal nicotine delivery system that can sustain a safe, effective dose of nicotine for 12 hours or more is not yet available, nor has a description of such a system been published.

SUMMARY OF THE INVENTION

The present invention is a transdermal patch that can hold and deliver sufficient nicotine to be effective for a period of 12 hours or more, preferably 24 hours. The patch therefore enables the major benefits of controlled-release drug delivery systems, such as steady blood plasma levels of nicotine, convenience, patient acceptance, reduced side effects, and so on, to be enjoyed by the user. These important advantages distinguish the present invention over the other types of nicotine patch already known in the art. The patch may take the form of a reservoir system, in which a depot of nicotine is separated from the skin by a non-porous polymeric membrane, through which the nicotine diffuses at a controlled rate. The patch may also be in the form of a monolithic matrix, consisting of a single phase solution or mixture of nicotine in a polymeric material, and wherein the nicotine is released by diffusion through the solution. A third possible embodiment involves a combined system from which nicotine is released by a combination of diffusion through a polymeric solution, and diffusion across a polymeric membrane. Embodiments employing a monolith of nicotine in a polymeric carrier are particularly preferred, because they offer yet other specific advantages not recognized by the prior art. First, the chemical activity of the nicotine is reduced, so that problems associated with skin irritation or attack of adhesive or other components are correspondingly reduced, and second, the nicotine is retained in such a way that it could not be released as a single burst, even if the patch were to be chewed or swallowed.

The patches of the present invention comprise a nicotine depot layer capable of holding the equivalent of the nicotine that would be absorbed by a smoker during a period of at least 12 or 24 hours. One side of this layer is in contact with an oclusive backing. The backing is nicotine-impermeable, and prevents loss of nicotine by evaporation to the surrounding environment during use. The other side of the layer faces the skin of the user. Depending on the particular embodiment, this layer may, but need not, be separated from direct contact with the skin by means of a polymeric membrane, a layer of medical tape, or a continuous or discontinuous adhesive layer. The third element of the patch is a means for controlling the rate of diffusion of nicotine from the patch. This means may take the form of a polymeric membrane, preferably non-porous, a polymeric solution in which the nicotine is dissolved or dispersed, or a combination of these.

The patches of the invention are normally attached adhesively to the skin of the user, although other attachment means that would hold the patch closely against the skin could be contemplated by the art.

It is an object of the present invention then to provide a transdermal nicotine patch that can replace one day's intake of nicotine through smoking.

It is a further object of the invention to provide a transdermal nicotine patch that is effective for periods of 12 hours or more.

It is a further object of the invention to provide a transdermal nicotine patch that can be used to treat patients suffering from nicotine addiction.

It is a further object of the invention to provide a transdermal nicotine patch that can satisfy a nicotine habit.

It is a further object of the invention to provide a transdermal nicotine patch that can hold one day's supply of nicotine.

It is a further object of the invention to provide a transdermal nicotine patch that can retain its nicotine load during prolonged periods of storage.

It is a further object of the invention to provide a transdermal nicotine patch that releases nicotine at an in vitro flux that is of the same order as the in vivo skin flux.

It is a further object of the invention to provide a transdermal nicotine patch that releases nicotine at an in vitro skin flux less than the in vivo skin flux.

It is a further object of the invention to provide a transdermal nicotine patch that avoids or minimizes overdose risks.

It is a further object of the invention to provide a transdermal nicotine patch that avoids or minimizes skin irritation.

It is a further object of the invention to provide a transdermal nicotine patch that avoids or minimizes component attack by nicotine.

It is a further object of the invention to provide a transdermal nicotine patch that can maintain steady blood plasma nicotine levels for prolonged periods.

It is a further object of the invention to provide a transdermal nicotine patch that reduces or eliminates morning craving in smokers.

It is a further object of the present invention to provide a transdermal nicotine patch that is readily acceptable to users.

It is a further object of the invention to provide a transdermal nicotine patch that is small and inconspicuous.

It is a further object of the invention to provide a transdermal nicotine patch that is replaced on a daily basis.

It is a further object of the present invention to provide a method of administering nicotine for non-smoking related therapeutic indications.

Further objects and advantages of the invention will be apparent from the description of the invention to those skilled in the art.

DETAILED DESCRIPTION OF THE INVENTION

"Nicotine" as used herein means pure nicotine or any compound thereof.

"Prolonged period" as used herein means about 12 hours or more.

"Monolith" as used herein means a single-phase combination of nicotine and a polymeric carrier.

Figure 1:
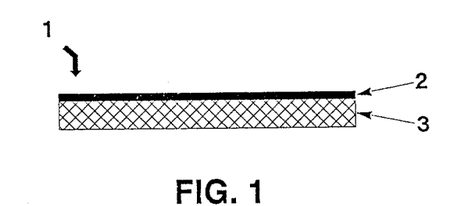
FIG. 1 shows an embodiment of the invention including an impermeable backing and a monolithic nicotine-containing matrix.

A basic embodiment of the present invention is shown in FIG. 1. Referring now to this figure, the nicotine dispensing patch, 1, comprises an impermeable backing layer, 2, and a monolithic matrix layer, 3, which both serves as a depot for the nicotine, and controls the rate at which it diffuses to the skin.

The impermeable backing layer, 2, defines the non-skin facing, or skin distal, side of the patch in use. The functions of the backing layer are to provide an occlusive layer that prevents loss of nicotine to the environment, and to protect the patch. The material chosen should therefore be nicotine resistant, and should exhibit minimal nicotine permeability. The backing layer should be opaque, because nicotine degrades when exposed to ultraviolet light. Ideally, the backing material should be capable of forming a support onto which the nicotine-containing matrix can be cast, and to which it will bond securely. A preferred material is polyester or aluminized polyester. Polyester has a nicotine permeability less than 0.2 μg.100 μm/cm².h. Preferred backings are polyester medical films, available for example from 3M Corporation as Scotchpak ® 1005 or 1109. While applicants believe that there are relatively few materials that are really sufficiently impermeable to nicotine to retain the nicotine load adequately during storage or use, other low permeability materials that might be tried include, for example, metal foil, metallized polyfoils, composite foils or films containing polyester, Teflon(polytetrafluoroethylene)-type materials or equivalents thereof that could perform the same function. As an alternative to casting the matrix directly on the backing, the polymer matrix may be cast separately and later stuck to the backing layer.

The nicotine monolith layer, 3, comprises nicotine finely dispersed, or preferably dissolved, in a polymer matrix. The monolith layer may be prepared as follows. First a solution of the polymer matrix material is made. Nicotine, preferably liquid, is then added to the polymer solution, and the mixture is homogenized. The percentage by weight of nicotine in the solution may be varied according to the desired loading of the finished monolith. The upper limit on the amount of nicotine that can be incorporated is determined by the stability of the solution. Above about 50 wt % nicotine, the monolith becomes a solution of the polymer in nicotine, rather than nicotine in the polymer, and depending on the polymer used, a point is reached where it is no longer possible to cast a stable film, because the solution remains in gel form or fluid form after casting. The monolith solution may be poured into a mold or cast alone or on the desired backing material. The casting is then covered, and left for the solvent to evaporate at room temperature. After solvent evaporation, the monolith takes the form of a polymer film typically having a thickness in the range about 50 to 800 μm. It will be appreciated that for a given desired total nicotine load, the percentage loading may be varied by varying the monolith thickness. In embodiments where the monolith is formed apart from the backing layer, a backing may be provided, for example, by attaching a layer of single-sided occlusive medical adhesive tape to one face of the cast film. The total nicotine content of the monolith will be sufficient to provide one day's supply. This amount depends on the user's need for nicotine. As a rough guide, a delivered load somewhere between 5 mg and 50 mg may be appropriate in smoking cessation therapy, although patches with a smaller load might be needed if the patient is almost weaned off nicotine, if only partial replacement of smoking is desired, or if the patch is indicated for some other therapeutic application than smoking cessation. It is probably not desirable to go above about 50 mg delivered nicotine content, because of the toxicity hazard, although in theory patches of this type with a bigger load can be made. Also, the amount of nicotine in the patch as made may exceed the delivered load. This is because, as the patch becomes exhausted, there will be an insufficient concentration gradient to remove all the nicotine, and consequently, the activity of the patch may fall below useful levels.

A feature of these monolith embodiments is that they provide a solution to the problems of skin irritation and potential toxicity. The activity of nicotine on the skin will be representative of the concentration of nicotine in the monolith. Thus a monolith with a nicotine content of 30 wt % will exhibit the activity of a 30 % solution, rather than pure nicotine, on the skin, with consequent substantial reduction or elimination of skin irritation. The release mechanism for the nicotine is diffusion under a concentration gradient. Therefore, even if the patch were to be ingested, the nicotine release would be still a gradual process, and the victim would not be exposed to a very large, toxic or lethal unit dose. Systems where the nicotine is held in an absorbent material, or mixed in with some other liquid or gel, do not have this advantage.

To ensure that a user cannot be exposed to a toxic dose when the patch is used correctly, the in vitro nicotine flux from the patch must stay within certain limits. This is a much more critical issue with nicotine than with most drugs, because nicotine is both very skin permeable, very toxic and very irritating. This can be understood if the average penetration rates of other transdermally administered agents through the skin are compared with nicotine. For example, nitroglycerin has a skin flux of 10–25 $\mu g/cm^2.h$, scopolamine 2–8 $\mu g/cm^2.h$, estradiol 0.01–0.03 $\mu g/cm^2.h$, and clonidine 0.5 $\mu g/cm^2.h$. The skin flux of nicotine is about 100–300 $\mu g/cm^2.h$. It should be appreciated that these are very approximate figures. One of the recognized problems in the art is that skin permeabilities can vary 20-fold or more between individuals and between different skin sites on the same individual. Therefore, in the case of nitroglycerin for example, a rare individual having a skin permeability 10 times greater than the average, using a transdermal system with an in vitro flux as great, or greater than the skin permeability, would be exposed to 100–250 $\mu g/cm^2.h$ of drug. On the other hand, that same individual using a nicotine patch with an area of 10 $cm^2$, and an in vitro release of 2 $mg/cm^2.h$, could absorb 10 mg nicotine per hour, a substantial fraction of the lethal dose. It is thus clear that a patch with a large nicotine load must be able to control release of that load, such that the in vitro flux from the patch does not exceed about 10 times, preferably about 5 times, and more preferably about equals, the average skin permeation rate. Of course, embodiments where the in vitro flux from the patch is less than the skin permeation rate, such that the systemic absorption is controlled primarily by the patch rather than the skin, are acceptable, so long as the systemic nicotine level can be sustained above the necessary minimum level for that individual's needs.

Polyurethanes are the preferred polymers for forming the monolith film, because they have been found to form stable solutions with nicotine, and they exhibit suitable nicotine permeabilities. The polyurethane used may be a polyether or polyester type. Polyether-type polyurethanes are preferred, because in general they are more inert than polyester-types, and thus more appropriate for biomedical use. Polyether-type polyurethanes are typically made by reacting a hydroxyl-terminated polyether oligomer with a diisocyanate according to the reaction:

where R is a polyether group. This prepolymer is then further reacted with another diol where R is small, for example, 1,4-butanediol, to yield a thermoplastic, rubbery polymer, the properties of which can be tailored by adjusting the proportions of polyether and butane diols. Polymers of this type in grades approved for medical use may be purchased from Dow Chemical, Midland, Michigan, under the name Pellethane ®. Different hardnesses are available; the softer grades are generally desirable in the present context because they are easier to dissolve and handle. Solvents that may be used to dissolve polyurethane include tetrahydrofuran (THF, T425-4, Fischer Scientific, Springfield, New Jersey), dimethysulfoxide (DMSO), and dimethylformamide (DMF). Tetrahydrofuran is approved for use with medical materials so long as the residue remaining in the material after evaporation does not exceed 1.5 wt %. It is usually desirable to make the concentration of polyurethane in the solvent as high as possible, so that the quantity of solvent that has to be evaporated is minimized. Other polymers than polyurethane that can exhibit equivalent monolith forming and nicotine flux characteristics are intended to be within the scope of the present invention. Examples that might be used, depending on the desired nicotine load, film thickness, etc. include methacrylate polymers such as polymethyl methacrylate or polybutyl methacrylate, or ethylene-acrylic acid polymers, or functional equivalents.

Figure 2:
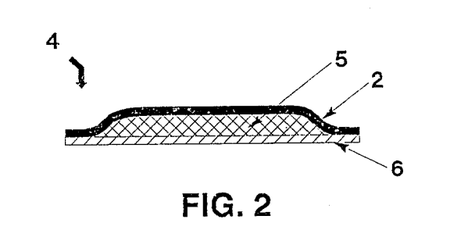
FIG. 2 shows an embodiment of the invention including an impermeable backing, a nicotine depot, and a rate-controlling polymer membrane.

Another embodiment of the invention is shown in FIG. 2. Referring now to this figure, the nicotine dispensing patch, 4, comprises an impermeable backing layer, 2, a nicotine reservoir, 5, and a polymer membrane, 6. The backing layer may be the same as that used for the monolith embodiment described above. The reservoir may take various forms, for example, pure nicotine, nicotine diluted with a liquid or gelled carrier, or nicotine contained within the pores of a microporous matrix. These reservoir systems are distinguished from the monolith embodiments of FIG. 1 in that the function of the reservoir layer is to be a depot for the nicotine and to keep it in good contact with the membrane layer. The reservoir layer does not contribute to any measurable extent to the rate-controlling mechanism. To discourage tampering with the patch, or misuse of the contents, it may be desirable to mix the nicotine with other materials as described in U.S. Pat. No. 4,597,961 to Etscorn, column 6, lines 1–10 incorporated herein by reference. If the patch is to be loaded with a comparatively small quantity of nicotine, such as would be needed to satisfy light smokers or for use during the latter stages of therapy, then the nicotine can be conveniently kept in contact with the membrane layer by holding it in the pores of a microporous matrix. Applicants have found that a disk of microporous nylon can be used. The disk also decreases the user's risk of exposure to a high dose of nicotine should the patch become accidentally ruptured. The polymer membrane layer, 6, is the rate-controlling means that regulates the flux of nicotine from the patch to the skin. The criteria for selection of a suitable material are those discussed in the background section above, namely resistance to attack by nicotine, and possession of an appropriate permeability for nicotine. The polymer chosen should also be compatible with the other components, and workable by standard techniques that are used in fabrication of the patch, such as casting or heat sealing. Dense non-porous membranes have a substantial advantage over microporous materials. Microporous membranes release the contents of the patch by pore flow. Thus, in the areas of the pores, the skin is exposed to raw nicotine. Also, in the case of a volatile liquid such as nicotine, flow through the pores occurs rapidly, so that the system is quickly exhausted, and the skin is flooded with excess nicotine for the life of the patch. In contrast, diffusion of nicotine through a non-porous film takes place by dissolution of the nicotine in the film, followed by diffusion under a concentration gradient. By selecting materials with suitable permeabilities, and making a membrane of appropriate thickness, it is possible, as taught by applicant, to tailor systems that can release their nicotine load gradually over 12 or 24 hours in a safe, controlled fashion. Furthermore, the solution/diffusion mechanism protects the patient's skin from exposure to excess amounts of raw nicotine. Based on extensive experimentation, applicants believe that preferred membranes polymers are low, medium or high density commercial polyethylenes. Particularly suitable are the grades obtainable under the trade name Sclairfilm ® from DuPont Canada or those from Consolidated Thermoplastics. Other possible membrane materials are polyamides, such as nylon 6,6, or some grades of ethylene vinyl acetate copolymers. Functional equivalents of these are intended to be within the scope of the invention. The membrane layer may be formed by preparing a solution of the chosen polymer in an organic solvent, casting on a glass plate or in a mold, and drying to evaporate the solvent. The thickness of the finished film is tailored to give the desired nicotine flux. In general, membranes used in transdermal patches have thickness ranging from about 5 $\mu$m to about 200 $\mu$m. Alternatively it may be possible to purchase the membrane already in film form. This type of transdermal patch may be prepared by heat-sealing the backing to the membrane layer around the perimeter of the patch. The nicotine formulation may be added either before or after heat sealing. If the formulation is added before heat sealing, it is convenient to shape the backing so as to form a cavity for retention of the nicotine, or to gel the nicotine. If the formulation is incorporated after heat sealing, the nicotine may be injected into the pouch formed by the heat sealing process, and the injection hole sealed.

As discussed for the monolithic embodiments, the patches of the present invention may frequently be required to hold a total nicotine load that is 50% or more of the lethal dose. It is therefore important that the patches be able to control the nicotine flux to the skin within safe limits at all times. In this regard, reservoir-type embodiments have an advantage over the monolith systems. The advantage is that, so long as undiluted nicotine remains in contact with the reservoir side of the membrane, the nicotine flux through the membrane remains relatively constant over the life of the patch. Monolith-type embodiments, on the other hand, often exhibit a falling flux with time, as the portion of the monolith closer to the skin becomes depleted of drug. As discussed above, these kinds of considerations matter more when dispensing nicotine than with many other substances. Suppose that a transdermal patch, tested in vitro, delivers a substantial fraction of its total drug load during the first few hours, at a flux several times higher than the average skin permeation rate. The in vitro flux then falls off to levels that are well below the average skin permeation rate until the patch is exhausted. When this patch is applied to a user, the skin will be saturated with drug and the drug will pass through the skin at a rate determined by that user's skin permeability. Typically a "depot" of drug will build up in the skin, and the drug will gradually reach the systemic circulation from this depot. Individuals with unusually high skin permeabilities will build up a larger skin depot faster than those with low skin permeabilities. For drugs that are less toxic than nicotine, less irritating to the skin, and/or have much lower skin permeabilities, this "skin depot" phenomenon may be perfectly acceptable, or even preferable, since it tends to balance out the falling flux from the patch. Many transdermal patches currently available exhibit this effect and function satisfactorily in this way. However, for nicotine, the situation is different. A patch that can avoid this high initial drug burst, with consequent skin irritation or risk of overdose, is desirable. Any initial flux from the patch should not exceed a maximum of 2 mg/cm$^2$.h, and more preferably should not exceed 1 mh/cm$^2$.h. Any flux this high should never be sustained for more than 4–5 hours, and preferably should not be sustained for more than 1–2 hours. Depending on the drug load, the skin permeability of the patient, and the drug flux required, it may be easier to stay within this limit with a reservoir-type patch. The risk of accidental overdose if the patch is damaged or ingested, however, is minimized with monolithic embodiments. There will therefore be circumstances where one or the other type of patch is preferably indicated.

Figure 3:
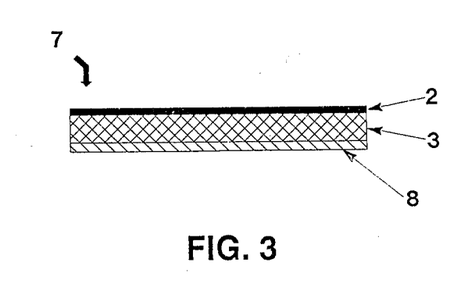
FIG. 3 shows an embodiment of the invention including an impermeable backing, a monolithic nicotine-containing matrix, and a polymer membrane.

As a way to exploit the advantages of both reservoir and monolith systems, applicants believe that a particularly preferred embodiment is that shown in FIG. 3. Referring now to this figure, the nicotine dispensing patch, 7, comprises an impermeable backing layer, 2, a monolithic matrix layer, 3, and a polymer membrane layer, 8. The backing and monolith layers are selected and prepared as described for the embodiment of FIG. 1. The membrane layer may be selected and prepared as described for the embodiment of FIG. 2. Alternatively, and preferably, the membrane layer may take the form of a double-sided medical adhesive tape, which may conveniently be attached to the finished monolith on the skin-facing side. If the tape contains a polymer backbone material that offers resistance to nicotine permeation, then this adhesive layer may have a nicotine permeability of the same order or less than the monolith material, so that the adhesive layer serves as a thin membrane limiting flux of nicotine from the patch. The system functions as a mixed monolith/reservoir system, where the nicotine release characteristic depend both on the monolith polymer and the membrane polymer. The preferred tapes for use in this way are those with a polyethylene backbone, such as 3M-1509, a 75 $\mu$m thick medical tape containing medium density polyethylene, and 3M-1512, a 38 $\mu$m thick polyethylene tape, both available from 3M Company. The additional resistance to permeation created by the tape assists in holding the nicotine load in the patch and moderates the initial high drug flux. This embodiment is particularly useful in cases where the percentage nicotine load of the monolith is high, say more than about 30 wt %, or where the total nicotine load is high, say 30 mg or more. Systems with this amount of nicotine are more likely to exhibit a large burst effect on initial application to the skin than those with low nicotine content. The additional resistance of the membrane/tape layer is useful in keeping the initial nicotine flux within therapeutically acceptable levels. Other advantages associated with this embodiment include a nicotine activity representative of the concentration of nicotine in the monolith, so that skin irritation and adhesive degradation are minimized. The risk of an overdose of nicotine is reduced, because the monolith cannot release its nicotine load in a single burst if the patch is damaged or even swallowed.

In use, the patches of the present invention may be held in contact with the skin of the user in a variety of ways, such as by means of a porous or non-porous overlay coated wholly or partly with adhesive, by an adhesive layer between the patch and skin, or by an annulus of adhesive around the periphery of the patch. Of course the mixed reservoir/monolith embodiments with adhesive medical tapes do not require additional adhesive.

If an adhesive layer is to be included as an integral part of the patch, the adhesive should be nicotine compatible and permit a useful nicotine flux. In addition, the adhesive should satisfy the general criteria for adhesives used for transdermal patches in terms of biocompatability, ease of application and removal, etc. Suitable adhesives for use in the practice of the invention include pressure-sensitive adhesives approved for medical use. Amine-resistant types are preferred, so that adhesive will not be attacked by the nicotine. A range of silicone-based amine-resistant medical adhesives is offered by Dow Corning under the trade name BIO PSA. Alternatively acrylate-type adhesives with amine resistance can be used. The adhesive layer can be cast directly onto the skin-facing side of the membrane or monolith as a thin film. Alternatively, medical adhesive tape, with or without nicotine-flux controlling properties, may be used.

Loss of nicotine from the patch after manufacture should be kept to a minimum. Normally, the skin-facing side of the patch will be covered with a peel strip until the patch is used. As stressed throughout, nicotine is volatile and retention of the nicotine load within the patch during storage requires that the outer layers are extremely nicotine-resistant and nicotine-impermeable. The peel strip therefore should possess the same properties as the backing layer, and the same materials are preferred.

The patches of the present invention enable smoking cessation therapy to be carried out by once-daily application of a transdermal patch. The total amount of nicotine released by the patch during that period will vary depending on the extent of the user's nicotine habit, but will be roughly in the range 5–50 mg, corresponding to smoking 5–50 cigarettes per day. The in vitro flux from the patch should remain below about 800 $\mu g/cm^2.h$, preferably below 600 $\mu g/cm^2.h$ and more preferably below 400 $\mu g/cm^2.h$ during the life of the patch. For useful total smoking cessation therapy, the minimum in vitro flux from the patch should be above 20 $\mu g/cm^2.h$ and preferably above 50 $\mu g/cm^2.h$ at all times. The most preferred flux range is 50–300 $\mu g/cm^2.h$. With large nicotine loads, it may not be possible to avoid some initial burst effect, but this burst flux from the patch should not exceed a maximum of 2 $mg/cm^2.h$ in vitro, and more preferably should not exceed 1 $mg/cm^2.h$ in vitro. Any flux this high should never be sustained for more than 4–5 hours, and preferably should not be sustained for more than 1–2 hours. Staying within these limits, and most preferaly keeping the nicotine flux below 800 $\mu g/cm^2.h$ throughout the use period, ensures that a patient with unusually permeable skin can never receive a toxic dose. The size of the patch will vary according to the amount of nicotine to be delivered. For an averge individual, nicotine flux through the skin is about 100–300 $\mu g/cm^2.h$. Therefore, to deliver 25 mg in a 24-hour period, the patch would have a sking-contacting area of about 3–10 $cm^2$. To maximize patient acceptance and compliance, and to minimize any skin irritation, the patch size should not exceed about 25 $cm^2$ maximum skin covering area. With the systems and release characteristics taught by applicant, it should be possible to keep the patch size in the range 1–20 $cm^2$, preferably 2–10 $cm^2$.

Other applications than to cure nicotine addiction are contemplated. For example, the patches of the invention may be used to help cut down, without eliminating, cigarette consumption, or to supply nicotine in a way that does not damage the lungs. In these cases, patches that deliver a smaller nicotine load, say 1–5 mg over 12–24 hours may be appropriate. There is some evidence in the literature that nicotine may have other therapeutic uses if it could be administered safely and effectively. For example U.S. Pat. No. 4,748,181 describes treatment of hypertension with nicotine, German Patent Publication DE No. 3438284 points out that nicotine is an appetite suppressant, and various other therapeutic properties have been ascribed to nicotine from time to time. It is envisaged that wherever therapeutic uses of nicotine might be found, a safe, convenient method of administration would be by means of the patches of the present invention.

The invention is now further illustrated by Examples 1 to 28, which are exemplary but non-limiting.

EXAMPLE 1 NICOTINE COMPATABILITY

The ability of a number of common polymers to withstand nicotine attack was assessed by soaking samples of the polymer in pure liquid nicotine for at least two days. The results are summarized in Table 1.

TABLE I

| Material | Observations and Remarks |
|---|---|
| ELVAX ® 40 (40% VAc) | attack and swelling |
| ELVAX ® 450 (18% VAc) | moderate swelling |
| ELVAX ® 650 (12% VAc) | very little swelling |
| ELVAX ® 750 (9% VAc) | no visible swelling or attack |
| ELVAX ® 880 (7.5% VAc) | no visible swelling or attack |
| Dartek ® F101 | no visible swelling or attack |
| Sclairfilm ® LWS-2-PA | no visible swelling or attack |
| Sclairfilm ® HD-2-PA | no visible swelling or attack |
| B410 (high-density polyethylene) | no visible swelling or attack |
| Hytrel ® 5556 | no visible swelling or attack |
| Saran ® 18L | color change, dissolves |
| Pellethane ® 70A | severe attack, dissolves |
| Pellethane ® 80AE | severe attack, dissolves |
| Estane ® 3714 | severe attack, dissolves |
| Poly(vinyl chloride) | |
| Polycarbonate | |
| Polystyrene | severe attack, dissolves |
| Glycol-modified poly-(ethylene terephthalate) | |
| Polybutyrate | |
| Mylar ® tape, 3M #1006 | stable, no visible attack |
| Release Liner, 3M #1022 | stable, no visible attack |

As can be seen, many materials swell, degrade or dissolve on exposure to nicotine.

Examples 2–6. Monolith Embodiments

EXAMPLE 2

Figure 4:
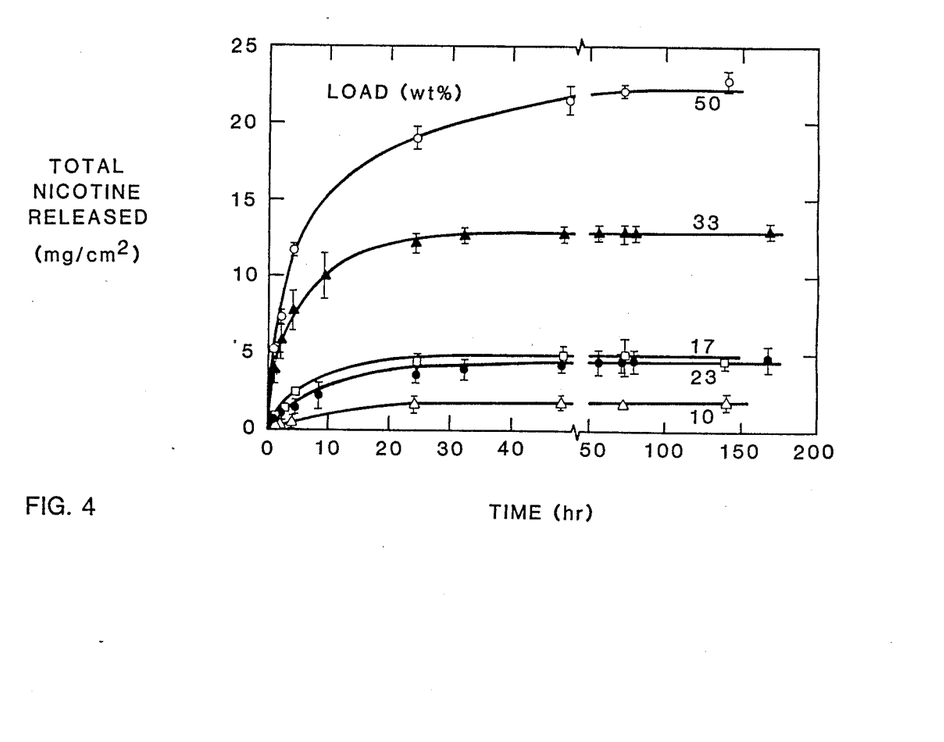
FIG. 4 is a graph of total nicotine release against time for a polyurethane/nicotine monolith.

Monolithic patches were made as follows. A solution of nicotine-loaded Pellethane 2363-80AE was made by mixing Pellethane pellets into tetrahydrofuran, adding 10 wt % liquid nicotine, and agitating on a bottle roller for three days. A layer of backing material grade 3M-1005 was spread in a petri dish and covered with the matrix mixture. The petri dish was covered, and the matrix was left for the solvent to evaporate at room temperature. Patches with an area of 3.88 $cm^2$ were cut from the finished matrix with a punch, and device release-rate measurements were made as follows. Each test device was suspended in a wire cage in an isotonic saline solution, constantly agitated by a magnetic stirrer, and maintained at 30° C. Periodic saline samples were taken for HPLC analysis using a Novapak C18 column. The results are given by the lowest curve in FIG. 4.

EXAMPLE 3

Monolithic patches were made and tested by the same procedure as described in Example 2, except that the nicotine content of the matrix mixture was 17 wt %. The results of the release tests are given by the second curve in FIG. 4.

EXAMPLE 4

Monolithic patches were made and tested by the same procedure as described in Example 2, except that the nicotine content of the matrix mixture was 23 wt %. The results of the release tests are given by the third curve in FIG. 4.

EXAMPLE 5

Monolithic patches were made and tested by the same procedure as described in Example 2, except that the nicotine content of the matrix mixture was 33 wt %. The results of the release tests are given by the fourth curve in FIG. 4.

EXAMPLE 6

Monolithic patches were made and tested by the same procedure as described in Example 2, except that the nicotine content of the matrix mixture was 50 wt %. The results of the release tests are given by the fifth curve in FIG. 4.

EXAMPLE 7. MEMBRANE FLUX TESTS

Promising membrane polymers that appeared to be able to withstand nicotine were tested for their nicotine permeability. The experimental procedure in each case was as follows. Samples of the films were mounted in teflon flow-through diffusion cells. Buffered isotonic saline was circulated through the bottom of the cell. Membrane samples were mounted on the bottom of each cell fixed by the threaded neck which also acts as the drug solution reservoir. The exposed area of the membrane was 3.9 cm$^2$. The membrane permeability was measured by the rate of permeation of nicotine into the saline solution. The samples were:
Dartek F101: nylon 6,6
Sclairfilm HD-2-PA: high density polyethylene
Sclairfilm LWS-2-PA: medium density polyethylene
Hytrel 5556: polyester elastomer
B410: high density polyethylene
ELVAX 880: ethylene/vinyl acetate copolymer, 7.5% vinyl acetate
Saran 18L: polyvinylidene chloride
The results are summarized in Table 2.

TABLE 2

| Membrane | Thickness ($\mu$m) | Nicotine Flux ($\mu$g/cm$^2 \cdot$ hr) | Nicotine Permeability ($\mu$g $\cdot$ 100 $\mu$m/cm$^2 \cdot$ hr) |
|---|---|---|---|
| Dartek ® F101 | 78 | 20 | 16 |
| Sclairfilm ® HD-2-PA | 22 | 60 | 27 |
| Sclairfilm ® LWS-2-PA | 50 | 45 | 22 |
| Hytrel ® 5556 | 250 | 10 | 25 |
| B410 | 50 | 20 | 10 |
| ELVAX ® 880 | 100–150 | >200 | >200 |
| Saran ® 18L | 50 | 16 | 8 |

Test conditions: 30° C. released into saline from 3.9-cm$^2$ test devices

Examples 8–15. Reservoir Embodiments

EXAMPLE 8

Figure 5:
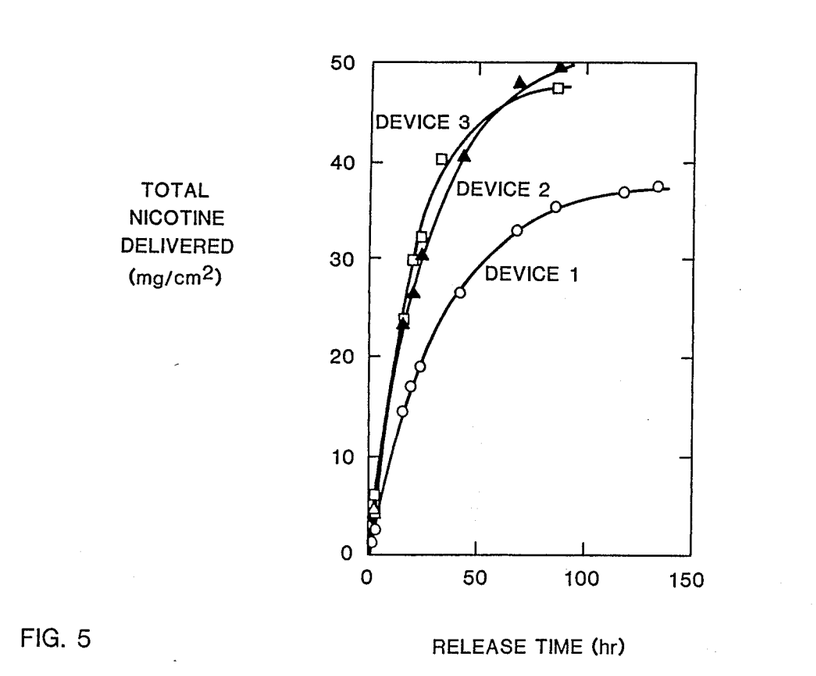
FIG. 5 is a graph of nicotine delivery through 100-micron thick Elvax 880 membranes, from a patch containing 200 μl pure nicotine, with a membrane area of 4.5 cm².

Experimental patches were made by heat sealing a backing of Scotch ® 1006 composite polyester tape to a 100-$\mu$m thick film of Elvax ® 880. The resulting pouches were filled with approximately 200 $\mu$l of nicotine, and the injection hole covered with a plug of hot melt glue. The finished patches had a membrane area of 4.5 cm$^2$. The release characteristics of the patches were tested by the procedure described in Example 2, and the nicotine was released into saline at 37° C. The results are given for three individual patches in FIG. 5. The patches exhibited very high initial fluxes of the order 2 mg/cm$^2$.h. Half the nicotine load was delivered within the first 15–20 hours.

EXAMPLE 9

Figure 6:
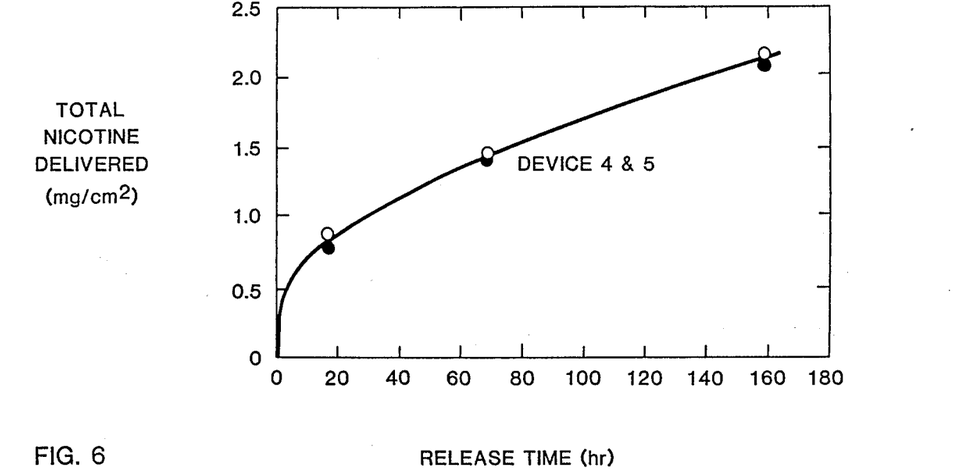
FIG. 6 is a graph of nicotine delivery through 100-micron thick Elvax 88 membranes, from a patch containing 200 μl of a 5% suspension of nicotine in a 20 wt % sodium sulfate solution, with a membrane area of 4.5 cm².

The patch-making procedure and release tests described in Example 8 were repeated using the same membrane, but with a load of 200 $\mu$ of 20 wt % sodium sulfate solution containing a 5% suspension of nicotine. The results are shown in FIG. 6. The patches exhibited a very high initial drug burst, followed by an average flux of about 8.5 $\mu$g/cm$^2$.h for the rest of the test period.

EXAMPLE 10

Figure 7:
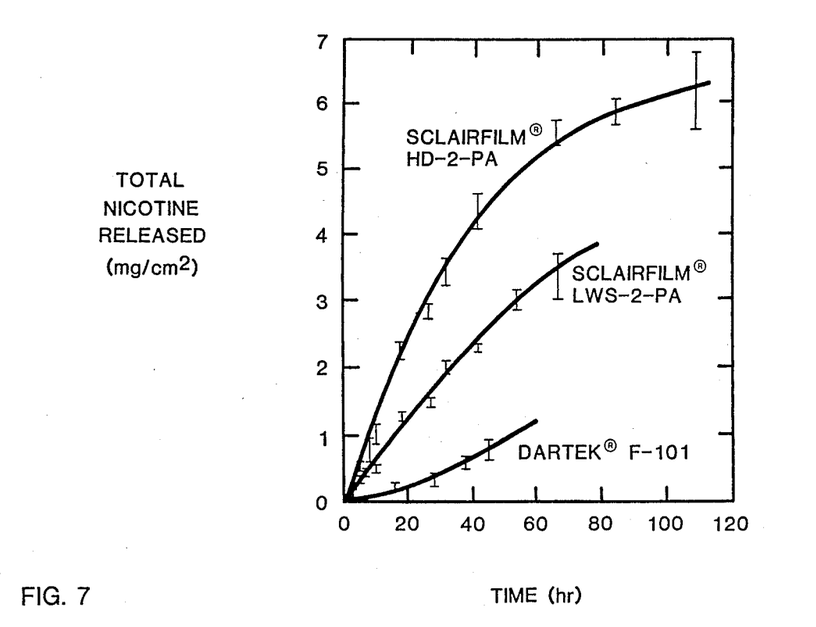
FIG. 7 is a graph of nicotine delivery from patches with nylon or polyethylene membranes. The nicotine content is 20–25 mg, and the patch area is 3.9 cm².

Experimental patches containing a disc of microporous nylon were made. A disc having an area of 3.9 cm$^2$ was punched from a sheet of microporous nylon 6,6. The disc was glued to a non-porous 78-$\mu$m thick film of Dartek F101 ®. The disc was wetted with nicotine. The disc could hold about 20–25 $\mu$l of nicotine. The membrane/disc assembly was heated sealed to a backing of Scotch ® 1006 or 1220 composite polyester tape. The finished patches had an effective membrane area of 3.9 cm$^2$. The release characteristics of the patches were tested by the procedure described in Example 1. The results of the release tests are given as the lowest curve in FIG. 7. The flux from these patches was about 10 $\mu$g/cm$^2$.h during the first 10 or 15 hours, rising to about 20 $\mu$g/cm$^2$.h after about 20–25 hours.

EXAMPLE 11

The patch-making procedure and relese tests described in Example 10 were repeated with a 22-$\mu$m thick film of Sclairfilm ® HD-2-PA as the membrane. The results are given as the upper curve in FIG. 7. The flux from the patch remained roughly constant at about 80 $\mu$g/cm$^2$.h for the first 60 hours, falling to about 30 $\mu$g/cm$^2$.h thereafter.

EXAMPLE 12

The patch-making procedure and release tests described in Example 10 were repeated with a 50-$\mu$m thick film of Sclairfilm ® LWS-2-PA as the membrane. The results are given as the middle curve in FIG. 7. The flux from the patch remained roughly constant at about 45–50 $\mu$g/cm$^2$.h.

EXAMPLE 13

Figure 8:
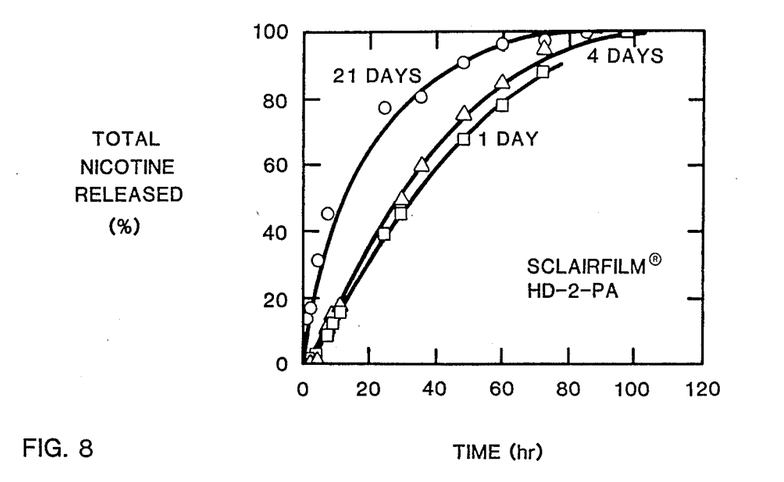
FIG. 8 is a graph of nicotine delivery from patches with high-density polyethylene membranes stored for 1, 4, or 21 days.

The patch-making procedure and release tests described in Example 11 were repeated after the test patches had been stored for periods of 1, 4, or 21 days. The results are given in FIG. 8. All the patches released their nicotine load more rapidly than did the patches that were tested soon after manufacture. The 1-day and 4-day stored patches exhibited a roughly constant flux for the first 40-50 hours. 40-50% of the total nicotine load was released in the first 25-30 hours. The 21-day stored patch exhibited a high initial burst effect and released 50% of its nicotine load in about the first 10 hours.

EXAMPLE 14

Figure 9:
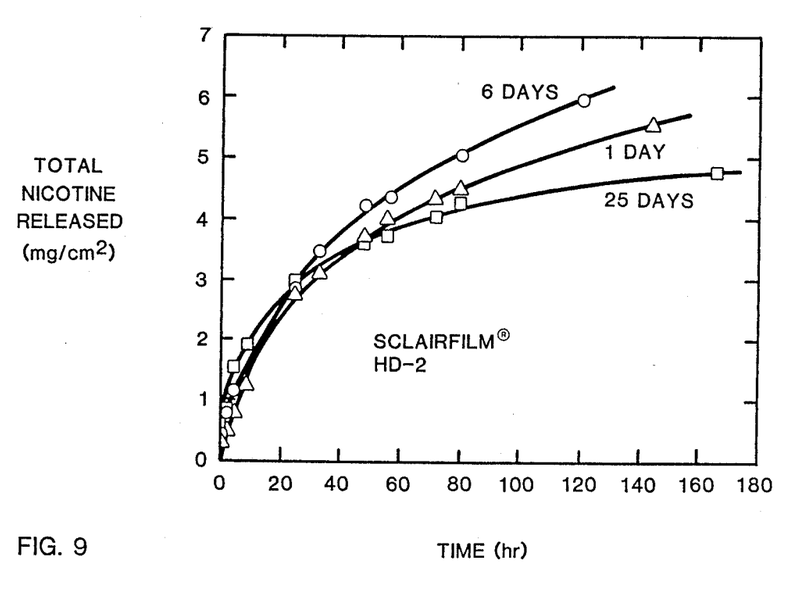
FIG. 9 is a graph of nicotine delivery from patches with high-density polyethylene membranes stored for 1, 6, or 25 days.

The patch-making procedure and release tests described in Example 11 were repeated using a 100-$\mu$m thick film of Sclairfilm ® HD-2-PA as the membrane, and storing the patches for 1, 6, or 25 days. The results are given in FIG. 9. The patches exhibited an initial flux of about 100 $\mu$g/cm$^2$.h, falling to about 50 $\mu$/cm$^2$.h. after about 30-40 hours.

EXAMPLE 15

Figure 10:
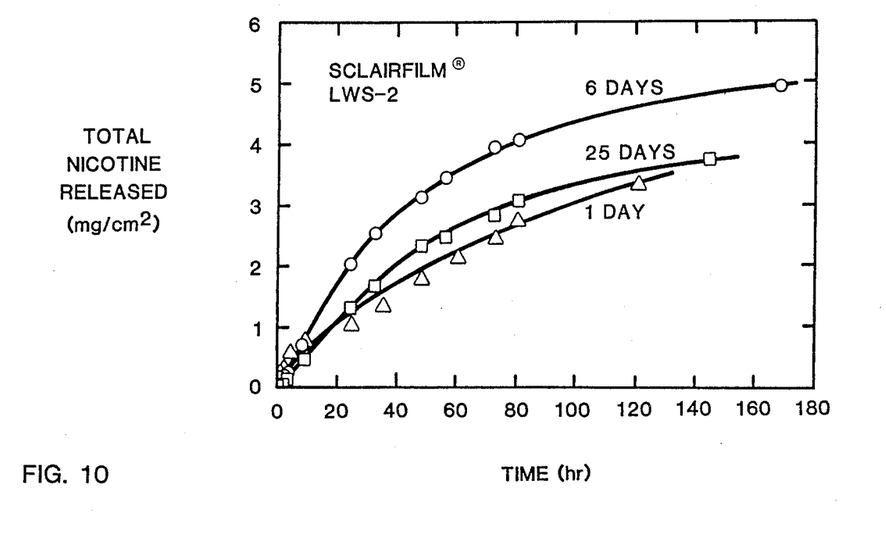
FIG. 10 is a graph of nicotine delivery from patches with medium-density polyethylene membranes stored for 1, 6, or 25 days.

The patch-making procedure and release tests described in Example 14 were repeated using a 50-$\mu$m thick film of Sclairfilm ® LWS-2-PA as the membrane, and storing the patches for 1, 6, or 25 days. The results are given in FIG. 10. The patches exhibited initial fluxes of about 50-90 $\mu$g/cm$^2$.h, falling to about 40-70 $\mu$g/cm$^2$.h after 40 hours.

Examples 16-18. Reservoir Embodiments with Adhesive

EXAMPLE 16

Figure 11:
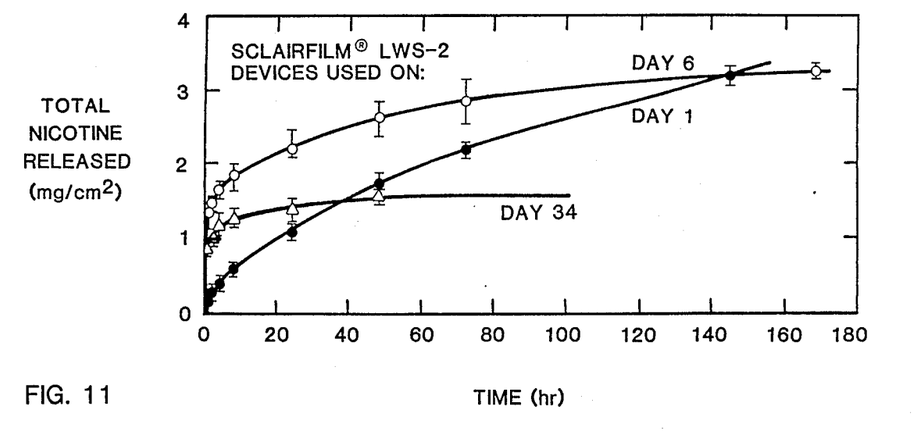
FIG. 11 is a graph of nicotine delivery from patches with medium-density polyethylene membranes and a 200-micron thick adhesive layer.

The patch-making procedure and release tests described in Example 15 were repeated. The patches were coated with a 200-$\mu$m thick film of BIO PSA grade X7-2920 adhesive, and stored for 1, 6, or 34 days. The results are given in FIG. 11. The patches exhibited a pronounced initial burst effect apparently as a result of migration of nicotine into the adhesive. The fluxes averaged over the first 8 hours for the 6-day and 34-day stored patches were in the range 160-230 $\mu$g/cm$^2$.h. As can be seen from the graph, the initial fluxes in the first couple of hours were much higher than this.

EXAMPLE 17

Figure 12:
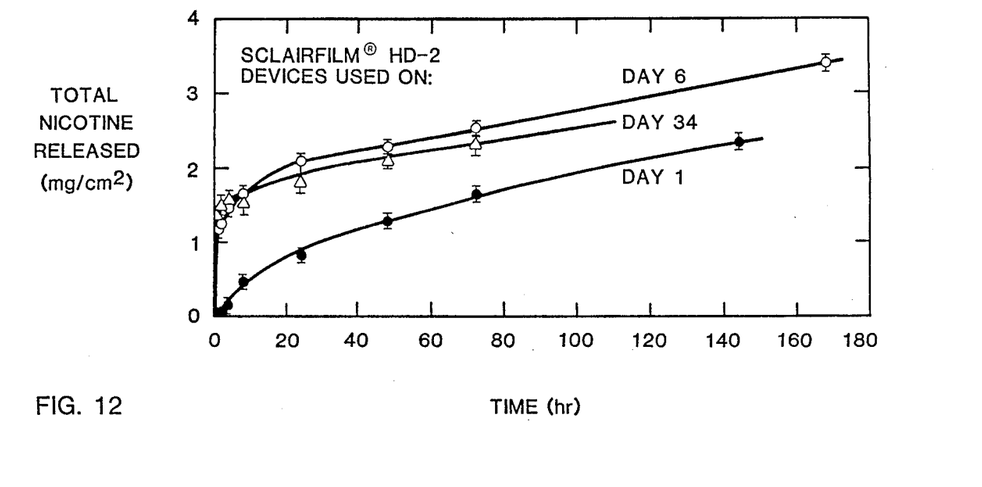
FIG. 12 is a graph of nicotine delivery from patches with high-density polyethylene membranes and a 200-micron thick adhesive layer.

The patch-making procedure and release tests described in Example 14 were repeated, using a 50-$\mu$m thick membrane, coating the patches with a 200-$\mu$m thick film of BIO PSA grade X7-2920 adhesive, and storing for 1, 6, or 34 days. The results are given in FIG. 12. As with Example 16, the patches exhibited a pronounced initial burst effect. The fluxes averaged about 200 $\mu$g/cm$^2$.h over the first 8 hours for the 6-day and 34-day stored patches. As the graph shows, the initial fluxes in the first couple of hours were very much higher.

EXAMPLE 18

Figure 13:
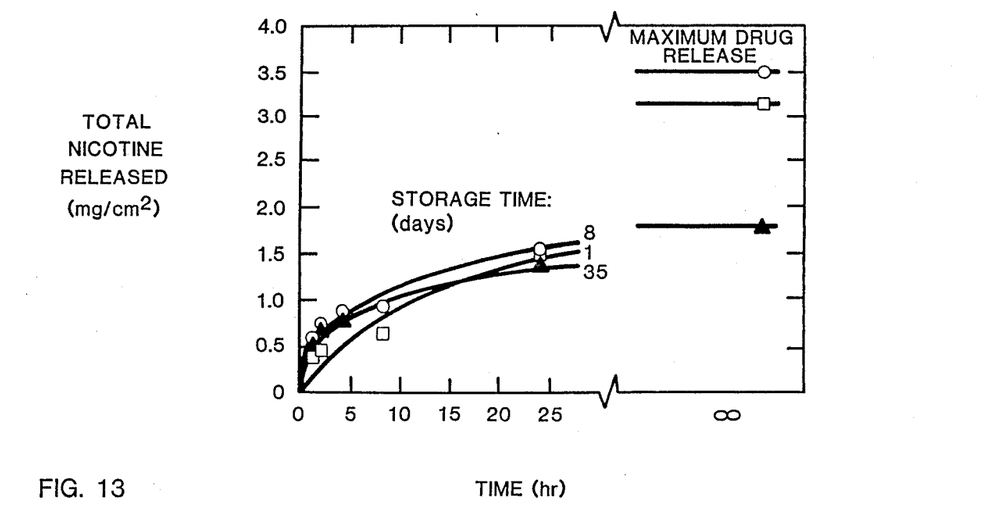
FIG. 13 is a graph of nicotine delivery from patches with high-density polyethylene membranes and a 25-micron thick adhesive layer.

The patch-making procedure and release tests described in Example 14 were repeated, using a 150-$\mu$m thick membrane, coating the patches with a 25-$\mu$m thick film of BIO PSA grade X7-2920 adhesive, and storing for 1, 8, or 35 days. The results are given in FIG. 13. With a thicker membrane, and a thinner layer of adhesive, the burst effect was substantially reduced. The fluxes for the 8-day and 35-day stored patches were both of the order 500 $\mu$g/cm$^2$.h for the first hours. The total nicotine released over the first five hours did not exceed 1 mg/cm$^2$.

Examples 19-28. Mixed Monolith/Membrane Systems

Monoliths containing 50% nicotine were made by the same general procedure as described in Example 2. For example 19, a membrane of 100-$\mu$m thick Sclairfilm ® HD-2-PA was cast onto the monolith. For example 20, a 38-$\mu$m thick membrane of polyethylene grade HD-106 obtained from Consolidated Thermplastics was cast onto the monolith. For examples 21 and 22, the membranes of examples 19 and 20 were coated with a 25-$\mu$m thick layer of BIO PSA grade X7-2920. For example 23, the monolith was coated with polyethylene, double-sided, medical adhesive tape grade 3M-1509. For example 24, the monolith was coated with polyethylene, double-sided, medical adhesive tape grade 3M-1512.

Figure 14:
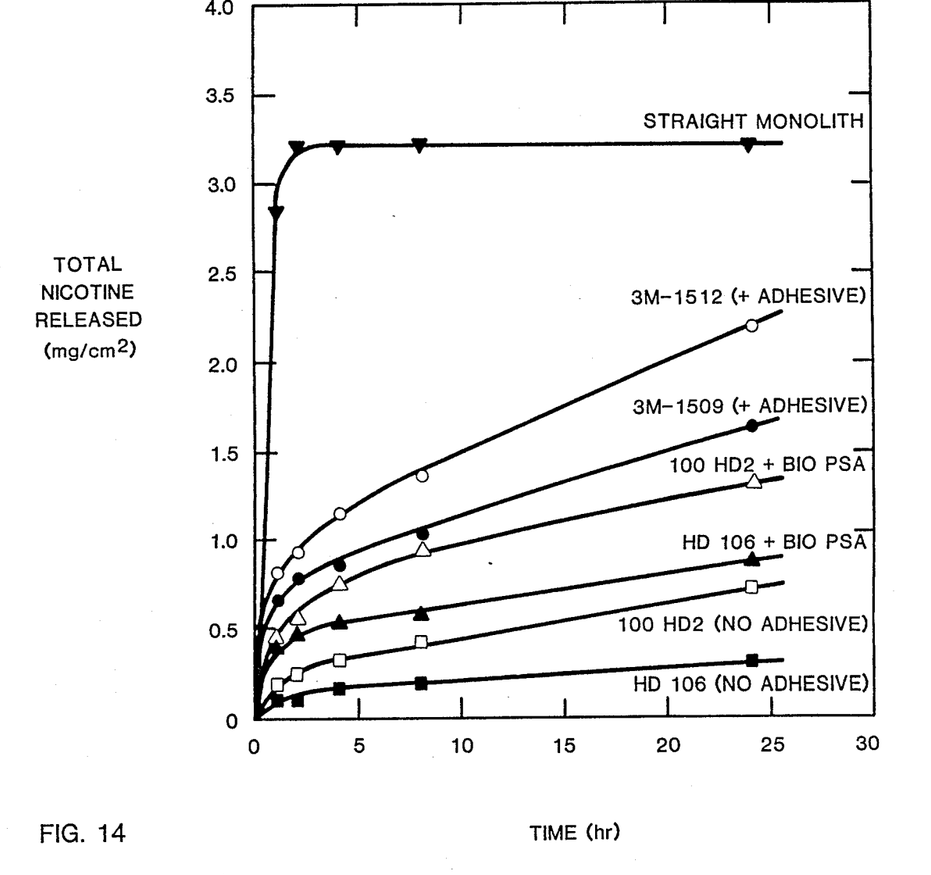
FIG. 14 is a graph of nicotine delivery from mixed monolith/membrane patches containing a 50% nicotine load, using a polyethylene membrane or a polyethylene medical tape.

Release tests were carried out as with the previous examples. The results for the various examples are given in FIG. 14. The upper curve shows the nicotine release from a monolith loaded with 50% nicotine without any membrane or adhesive. As can be seen, the presence of the membrane or membrane tape brings the steady-state flux down to 50 $\mu$g/cm$^2$.h or less.

EXAMPLES 25-28

Figure 15:
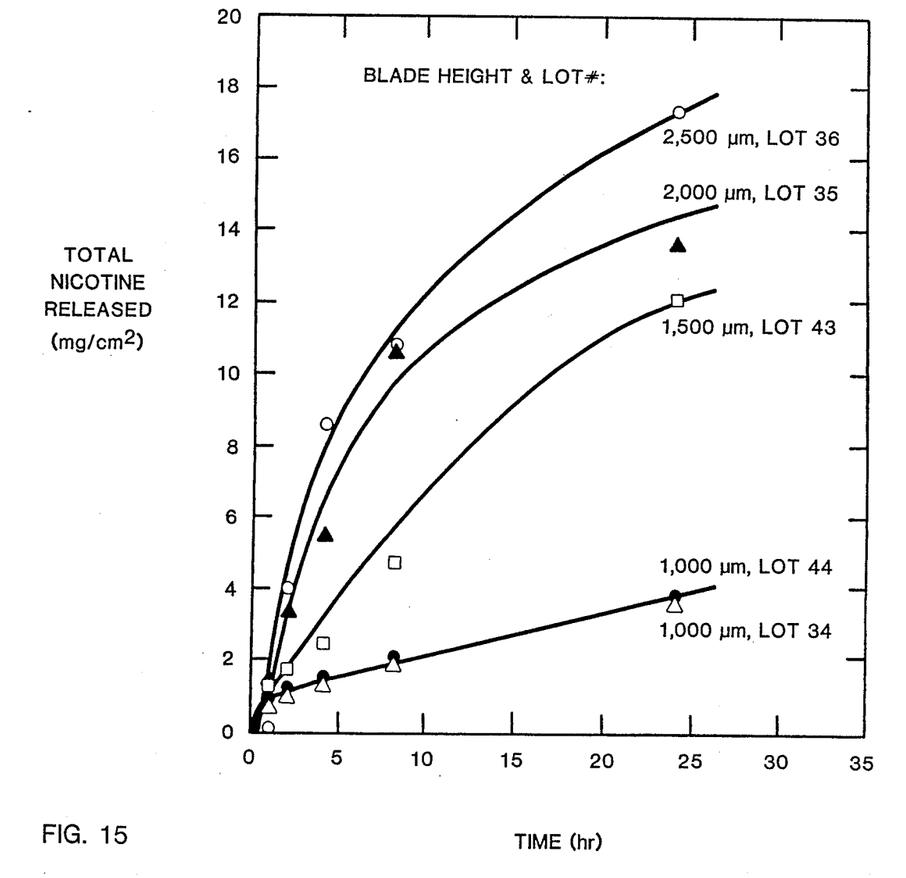
FIG. 15 is a graph of nicotine delivery from mixed monolith/membrane patches containing a 40% nicotine load, using a polyethylene membrane or a polyethylene medical tape.

Monoliths containing 40% nicotine were made by the same general procedure as described in Example 2. For example 25, the monolith was cast with the blade height set at 1,000 $\mu$m. For example 26, the monolith was cast with the blade height set at 1,500 $\mu$m. For example 27, the monolith was cast with the blade height set at 2,000 $\mu$m. For example 28, the monolith was cast with the blade height set at 2,500 $\mu$m. All monoliths were covered with 3M-1512 medical tape. Release tests were carried out as for the previous examples. The results are given in FIG. 15. A more pronounced burst effect was observed with the thicker monoliths, containing more nicotine. The 1,500 $\mu$m cast monolith maintained a average flux of about 500 $\mu$g/cm$^2$.h for 24 hours, and released a total of about 4 mg/cm$^2$ in the first 5 hours. The 1,000 $\mu$m cast monolith maintained an average flux of about 120 $\mu$g/cm$^2$.h for 24 hours, and released a total of about 1.5 mg/cm$^2$ in the first 5 hours.

We claim:
1. A transdermal patch, comprising:
    (a) A nicotine depot layer, having a skin-facing side and a skin-distal side, said depot layer containing a sufficient quantity of nicotine to maintain a useful flux of nicotine from said patch for a total time period of 12 hours or more;
    (b) an occlusive backing layer in contact with and covering said depot layer on said skin-distal side; and
    (c) rate-controlling means for controlling diffusion of nicotine from said skin-facing side at a first flux of greater than zero but less than 2 mg/cm$^2$ in any hour for a first time period of greater than zero but less than 5 hours, then at a second flux between 20 and 800 $\mu$g/cm$^2$.h for a second time period of 7 hours or more.
2. The patch of claim 1, wherein said rate-controlling means comprises a nicotine-permeable polymer mem- brane contacting said depot layer on said skin-facing surface.

3. The patch of claim 1, wherein said rate-controlling means comprises a nicotine-permeable polymer monolith integral with said depot layer.

4. The patch of claim 1, wherein said rate-controlling means comprises a combination of a nicotine-permeable polymer monolith integral with said depot layer and a nicotine-permeable polymer membrane contacting said depot layer on said skin-facing surface.

5. The patch of claim 1, wherein said depot layer comprises a porous material with said nicotine dispersed therein.

6. The patch of claim 2, wherein said membrane is made from polyethylene.

7. The patch of claim 3, wherein said monolith is made from polyurethane.

8. The patch of claim 4, wherein said membrane is double-sided medical adhesive tape.

9. The patch of claim 1, wherein said first flux is greater than zero but less than 1 mg/cm$^2$ in any hour.

10. The patch of claim 1, wherein said first time period is less than 1 hour, and said second time period is 11 hours or more.

11. A transdermal patch, comprising:
(a) a nicotine depot layer, having a skin-facing side and a skin-distal side, said depot layer containing a sufficient quantity of nicotine to maintain a useful flux of nicotine from said patch for a period of 12 hours or more;
(b) an occlusive backing layer in contact with and covering said depot layer on said skin-distal side; and
(c) rate-controlling means for controlling diffusion of nicotine from said skin-facing side at a flux between 20 and 800 μg/cm$^2$.h for a period of 12 hours or more.

12. A method of administering nicotine to an individual in need of such administration, comprising applying to the skin of said individual a transdermal patch, said patch comprising:
(a) a nicotine depot layer, having a skin-facing side and a skin-distal side, said depot layer containing a sufficient quantity of nicotine to maintain a useful flux of nicotine from said patch for a total time period of 12 hours or more;
(b) an occlusive backing layer in contact with and covering said depot layer on said skin-distal side; and
(c) rate-controlling means for controlling diffusion of nicotine from said skin-facing side at a first flux less 2 mg/cm$^2$.h for a first time period less than 5 hours, then at a second flux between 20 and 800 μg/cm$^2$.h for a second time period of 7 hours or more.

13. The method of claim 12, wherein said rate-controlling means comprises a nicotine-permeable polymer membrane contacting said depot layer on said skin-facing surface.

14. The method of claim 12, wherein said rate-controlling means comprises a nicotine-permeable polymer monolith integral with said depot layer.

15. The method of claim 12, wherein said rate-controlling means comprises a combination of a nicotine-permeable polymer monolith integral with said depot layer and a nicotine-permeable polymer membrane contacting said depot layer on said skin-facing surface.

16. The method of claim 12, wherein said depot layer comprises a porous material with said nicotine dispersed therein.

17. The method of claim 1, wherein said membrane is made from polyethylene.

18. The method of claim 14, wherein said monolith is made from polyurethane.

19. The method of claim 15, wherein said membrane is double-sided medical adhesive tape.

20. The method of claim 12, wherein said first flux is less than 1 mg/cm$^2$.h.

21. The method of claim 12, wherein said first time period is less than 1 hour, and said second time period is 11 hours or more.

22. A method of administering nicotine to an individual in need of such administration, comprising applying to the skin of said individual a transdermal patch, said patch comprising:
(a) a nicotine depot layer, having a skin-facing side and a skin-distal side, said depot layer containing a sufficient quantity of nicotine to maintain a useful flux of nicotine from said patch for a period of 12 hours or more;
(b) an occlusive backing layer in contact with and covering said depot layer on said skin-distal side; and
(c) rate-controlling means for controlling diffusion of nicotine from said skin-facing side at a flux between 20 and 800 μg/cm$^2$.h for a period of 12 hours or more.

* * * * *